United States Patent
Riddell

(10) Patent No.: US 7,168,122 B1
(45) Date of Patent: Jan. 30, 2007

(54) RECIPROCATING GERMICIDAL TOOTHBRUSH AND SYSTEM

(76) Inventor: Robert H. Riddell, 4711-116th Ave. SE., Bellevue, WA (US) 98006

( * ) Notice: Subject to any disclaimer, the term of this patent is extended or adjusted under 35 U.S.C. 154(b) by 0 days.

(21) Appl. No.: 11/329,811

(22) Filed: Jan. 10, 2006

(51) Int. Cl.
*A46B 13/00* (2006.01)

(52) U.S. Cl. .................. 15/22.1; 15/105; 15/167.1; 433/29

(58) Field of Classification Search .............. None
See application file for complete search history.

(56) References Cited

U.S. PATENT DOCUMENTS

| | | | |
|---|---|---|---|
| 3,261,978 A | 7/1966 | Brenman | 250/86 |
| 4,253,212 A | 3/1981 | Fujita | 15/167 |
| 5,030,090 A | 7/1991 | Maeda et al. | 433/29 |
| D394,133 S | 5/1998 | Mead | D32/35 |
| 5,813,855 A | 9/1998 | Crisio, Jr. | 433/29 |
| 6,106,294 A | 8/2000 | Daniel | 433/216 |
| 6,202,242 B1* | 3/2001 | Salmon et al. | 15/22.1 |
| 6,752,627 B2* | 6/2004 | Lin | 433/29 |
| 6,862,771 B1* | 3/2005 | Muller | 15/105 |
| 6,954,961 B2* | 10/2005 | Ferber et al. | 15/22.1 |
| 2005/0172429 A1* | 8/2005 | Russell et al. | 15/22.1 |
| 2005/0175956 A1* | 8/2005 | Russell et al. | 433/29 |
| 2005/0271997 A1* | 12/2005 | Mikami et al. | 433/29 |

* cited by examiner

Primary Examiner—David Redding
(74) Attorney, Agent, or Firm—Dean A. Craine

(57) ABSTRACT

A germicidal toothbrush that includes a head with perpendicularly aligned bristles made of an optical fiber capable of transmitting germicidal ultraviolet light. The toothbrush includes a main optical fiber that extends longitudinally inside the handle and terminates inside a brush head cavity. Perpendicularly aligned and attached to the brush head is a plurality of bristles. The distal end of the main optical fiber includes a sloped surface so that coherent ultraviolet light may be emitted at a critical angle so that it enters the ends of the bristles and then travels longitudinally therein to the surrounding teeth and gum surfaces. The ends of the bristles are coupled to a metal bar that connects to a connecting rod. The connecting rod is coupled to an internal electric motor that that causes the bristles to reciprocate back and forth on the head.

18 Claims, 7 Drawing Sheets

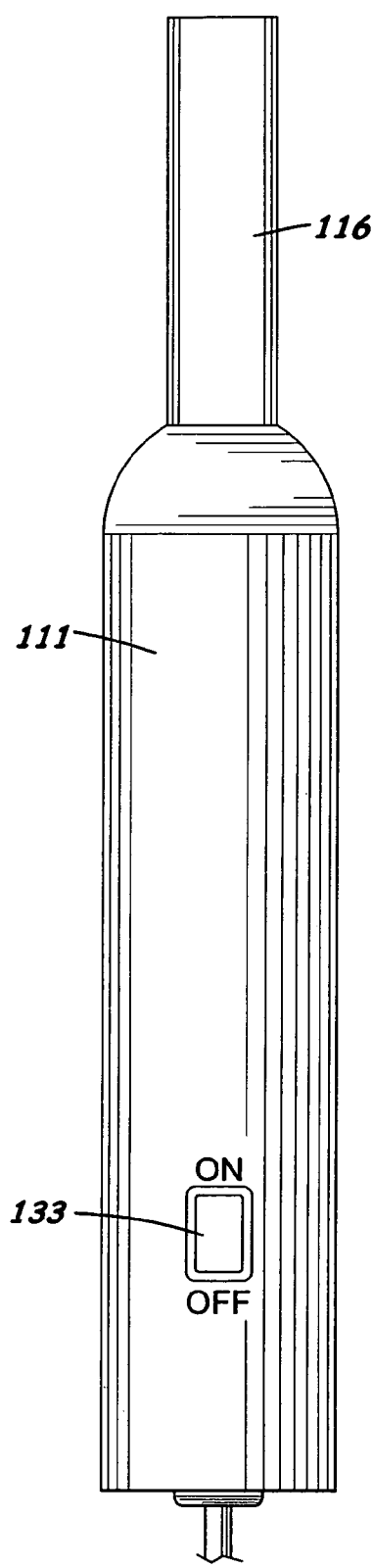
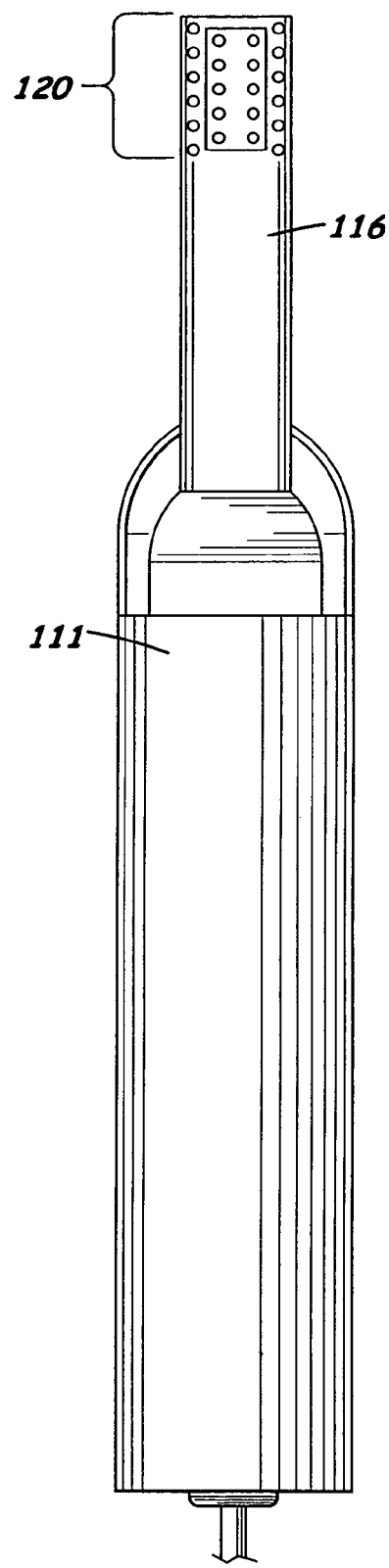
Fig. 3
Fig. 4

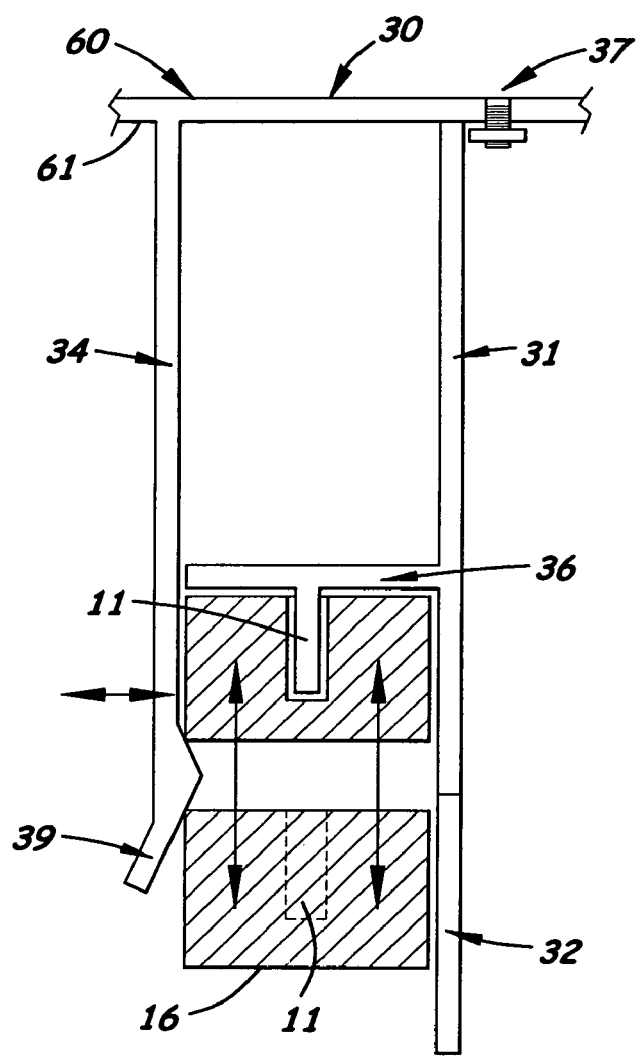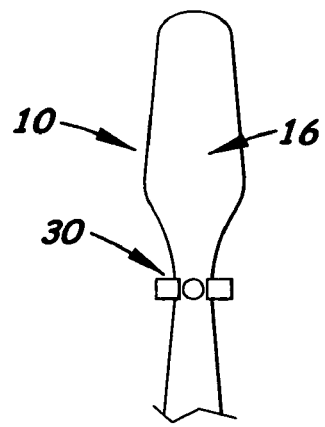
Fig. 12
Fig. 13

RECIPROCATING GERMICIDAL TOOTHBRUSH AND SYSTEM

BACKGROUND OF THE INVENTION

1. Field of the Invention

This invention relates to electric toothbrushes, and more particularly to electric toothbrushes that include bristles made of a fiber optic that reciprocates on the brush head.

2. Description of the Related Art

Electric toothbrushes typically include a head that rocks back and forth or a plurality of bristles that rotate continuously or twist back and forth over the surfaces of the teeth or gums. One drawback with such toothbrushes is that the bristles do not adequately clean the gum pockets formed on the sides of the teeth.

Toothbrush cleaners that use ultraviolet light to clean the bristles and heads of a toothbrush are disclosed in the inventor's previously filed U.S. utility patent application GERMICIDAL TOOTHBRUSH AND HOLDER, (Ser. No. 10/865,877), filed on Jun. 14, 2004. Such cleaners, which are incorporated by reference herein, include a germicidal ultraviolet light source that produces coherent ultraviolet light of a suitable wavelength (254 nm) capable of acting as a germicide.

SUMMARY OF THE INVENTION

It is an object of the present invention to provide a toothbrush with bristles made of an optical fiber capable of transmitting germicidal ultraviolet and near infrared light to the teeth and gums.

It is another object of the present invention to provide a toothbrush that connects to an external ultraviolet and near infrared light source.

It is another object of the present invention to provide such a toothbrush that includes a plurality of brushes that move longitudinally in a reciprocating manner on the head of the toothbrush.

These and other objects are met by the toothbrush disclosed therein that includes a toothbrush with a head having a plurality of perpendicularly aligned bristles some or all made of an optical fiber. Each bristle is designed to transmit germicidal ultraviolet and near infrared light to the teeth and gums during use. The toothbrush includes an elongated hand piece with a main optical fiber longitudinally aligned and disposed therein that extends from the distal end of the hand piece to a cavity formed inside the head. The distal end of the optical fiber terminates at a location and behind the proximal end of the bristles that extend into the cavity formed in the head. The proximal end of the main optical fiber terminates at a suitable angle relative to the ends of the bristles so that ultraviolet light and near infrared light transmitted through the optical fiber is optimally transmitted to the proximal ends of the bristles. In the preferred embodiment, the main optical fiber has a sloped distal end surface so that the light from the main optical fiber is emitted at a critical angle for transmission into the ends the bristles that are perpendicularly aligned with the bristles longitudinally axis. Some or all of the bristles are also made of an optical fiber capable of transmitting light emitted from the distal end of the main optical fiber to the teeth and gum tissues surrounding the bristles.

The proximal ends of some or all of the bristles on the toothbrush head are coupled to a longitudinally metal bar that moves longitudinally inside the upper portion of the hand piece and the head. The metal bar is connected to a gear assembly located inside the hand piece. The gear assembly is coupled to an electric motor connected to a D.C. power source and to a manual switch mounted on the sides of the hand piece that controls operation of the electric motor.

The distal end of the main optical fiber extends from the lower end of the hand piece and connects to a snap connector attached to a primary optical fiber cable. The primary optical fiber connects to a light box containing either an ultraviolet light source, or a near infrared light source, or both. The primary optical fiber may contain a single optical fiber or contain a plurality of optical fibers bundled together all capable of transmitting both ultraviolet and infrared light. The primary optical fiber may also include two separate sets of different optical fibers capable of transmitting only ultraviolet or only infrared light. The light box includes a main ON/OFF switch and a timer that controls the operation of the two light sources housed therein.

DESCRIPTION OF THE DRAWINGS

FIG. 3 is a rear elevational view of the toothbrush.

FIG. 4 is a front elevational view of the toothbrush.

FIG. 12 is a sectional, top plan view of a toothbrush being mounted on a toothbrush clip.

FIG. 13 is a front plan view of a toothbrush being mounted on a toothbrush clip.

DESCRIPTION OF THE PREFERRED EMBODIMENT(S)

Figure 1:
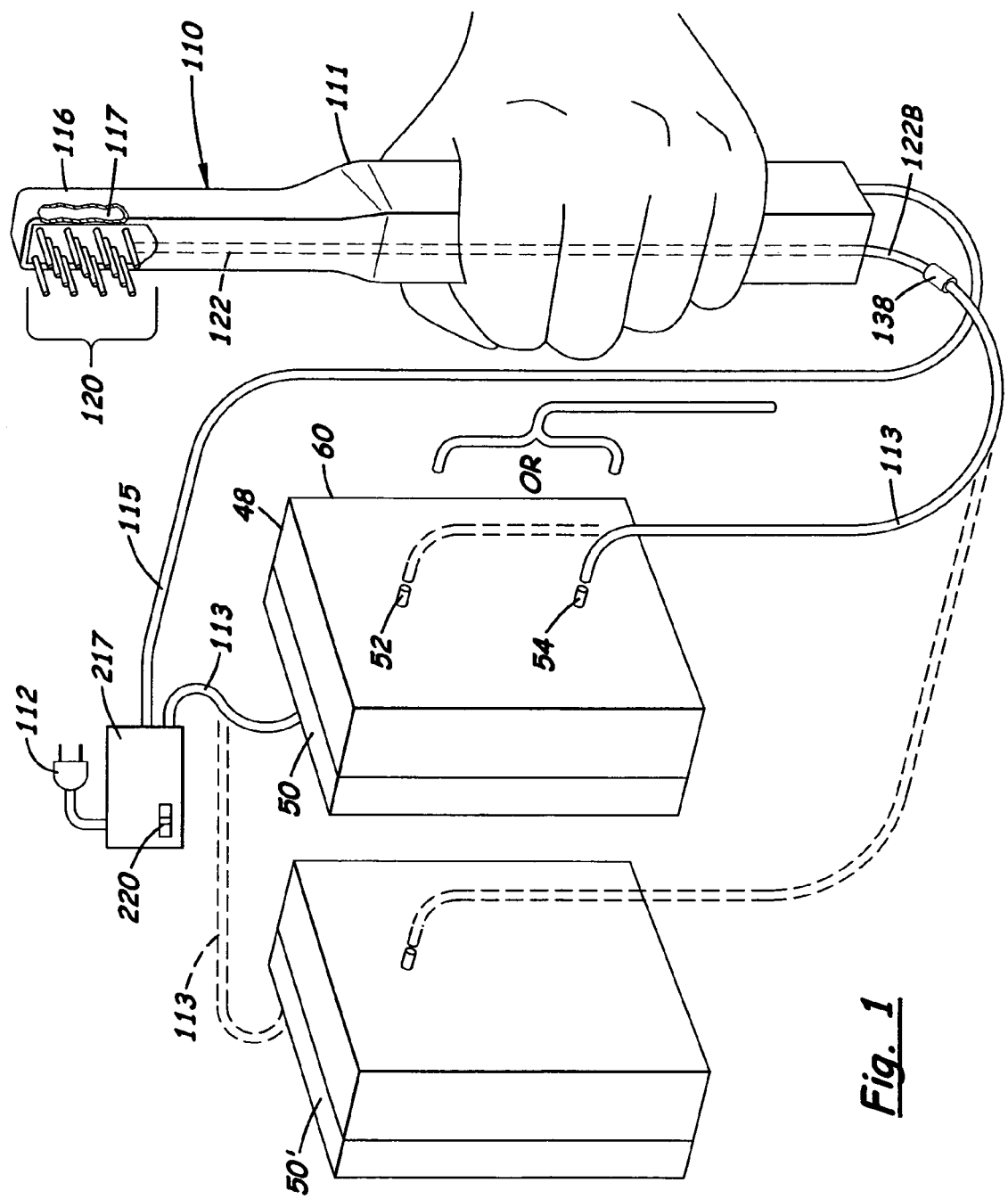
FIG. 1 is a perspective view of the reciprocating germicidal toothbrush system.
Figure 2:
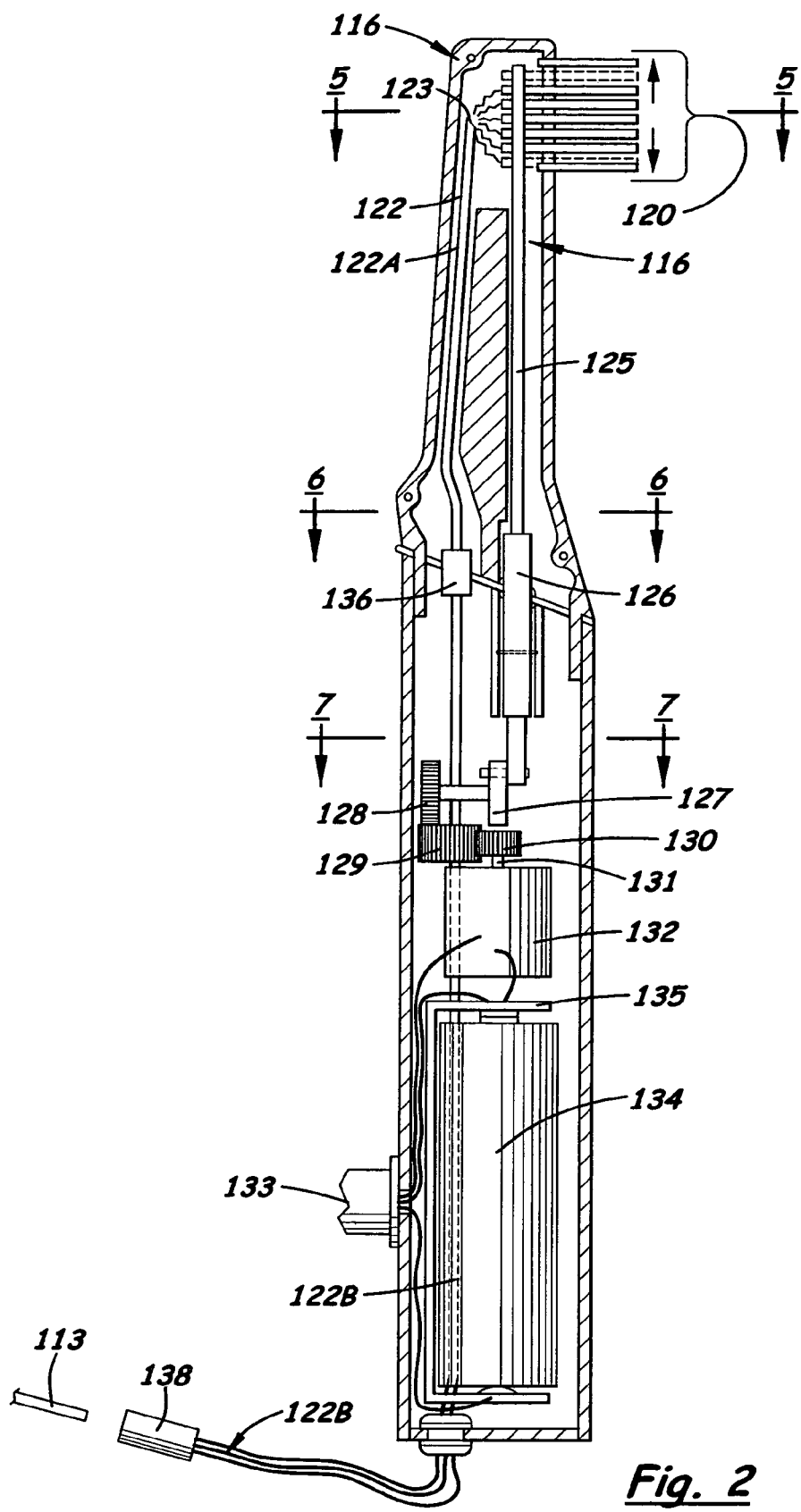
FIG. 2 is a sectional side elevational view of the toothbrush.
Figure 5:
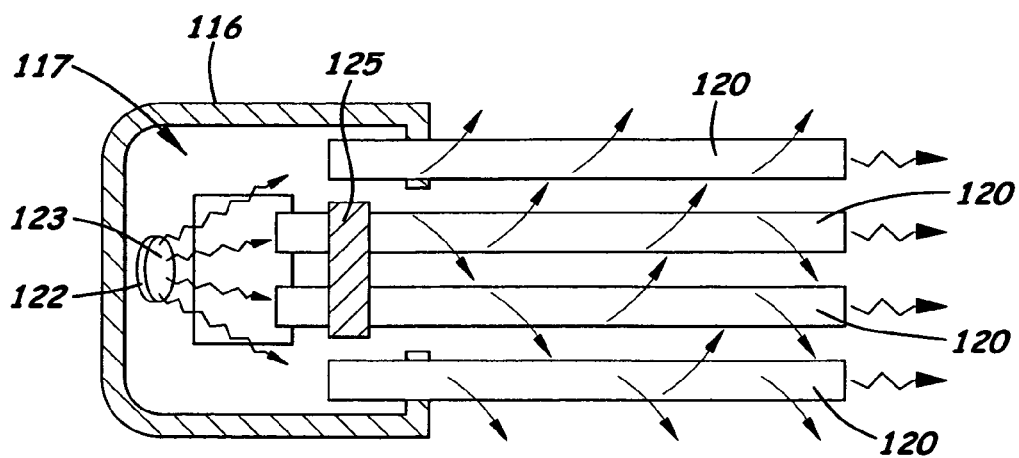
FIG. 5 is a sectional, side elevational view of the head of the toothbrush taken along line 5—5 in FIG. 3.
Figure 6:
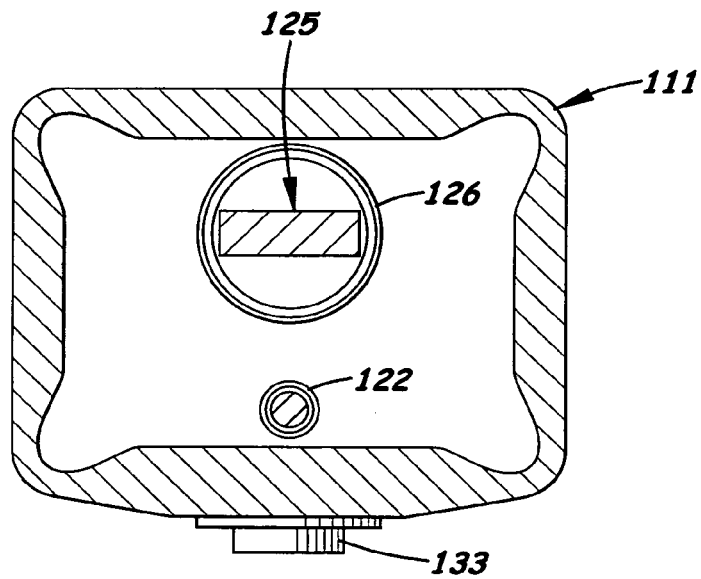
FIG. 6 is a sectional, side elevational view of the toothbrush taken along line 6—6 in FIG. 3.
Figure 7:
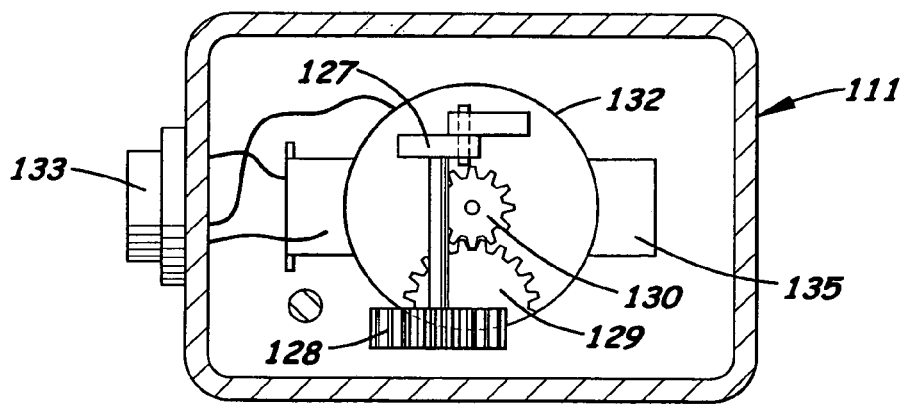
FIG. 7 is a sectional, side elevational view of the toothbrush taken along line 7—7 in FIG. 3.

Shown in the accompanying Figs there is shown an electrical reciprocating germicidal toothbrush 110 that includes a head 116 with a plurality of perpendicularly aligned bristles 120 each made of a bare or cladded optical fiber capable of transmitting germicidal ultraviolet light and near infrared light. The toothbrush 110 includes an elongated hand piece 111 with a removable head 116. Located inside the hand piece 111 is a longitudinally aligned main optical fiber 122 that extends from one end of the hand piece 111 and terminates inside a cavity 117 formed in the head 116. As shown in FIGS. 1 and 2, the distal end 123 of the main optical fiber 122 is positioned inside the cavity 117 and is sloped so that ultraviolet and near infrared light emitted from the distal end 123 at a critical angle capable to entering the flat, perpendicularly aligned proximal ends of the bristles 120 that extend into the cavity 117. During operation, the bristles 120 internally reflex the ultraviolet light and near infrared light delivered via the main optical fiber 122 and emit ultraviolet and near infrared light onto the surrounding teeth and gum tissue.

In the preferred embodiment, the bristles 120 are attached to an optional reciprocating means designed to move some or all of the bristles 120 in a fore and aft direction inside the head 116. In the preferred embodiment, the reciprocating means is a longitudinally aligned metal bar 125, a longitudinally aligned connecting rod 126, and an electric motor 130. The bristles 120 are perpendicularly aligned and attached at their distal ends to the distal end of the metal bar 125. The proximal end of the metal bar 125 is connected to the distal end of the connecting rod 126. The proximal end of the connecting rod 126 is coupled via a linkage assembly 127 in an offset position to a rotating main gear 128. When the main gear 128 rotates, the linkage assembly 127 rotates which causes the connecting rod 126 to move longitudinally inside the head 116 and the hand piece 111. The main gear 128 meshes with a drive gear 129 that in turn, meshes with a pinion gear 130 attached to the drive shaft 131 on an electric motor 132 also located inside the hand piece 111. The electric motor 132 is connected to a switch 133 mounted on the side of the hand piece 111. An optional battery 134 is longitudinally aligned inside the hand piece 111 and inserted into a battery-receiving cradle 135. The positive and negative ports on the cradle 135 are connected to the switch 133 and the electric motor 132.

The main optical fiber 122 which extends longitudinally inside the hand piece is divided into two sections a head fiber section 122A, and a hand piece fiber section 122B. The head fiber section 122A is longitudinally aligned inside the head 116. The distal end of the head fiber section 122A terminates inside the cavity 117 while the opposite proximal end extends through the end of the head 116 and connects to a first coupler 136 attached to the distal end of the hand piece fiber section 122B. The distal end of the hand piece fiber section 122B extends from the hand piece 111 and connects the first coupler 136. The proximal end of the hand piece fiber section 122B extends from the proximal end of the hand piece 111 and connects to a second coupler 138 used to connect to a primary optical fiber 113. The primary optical fiber 113 connects to an ultraviolet and infrared light source as described further below.

Figure 8:
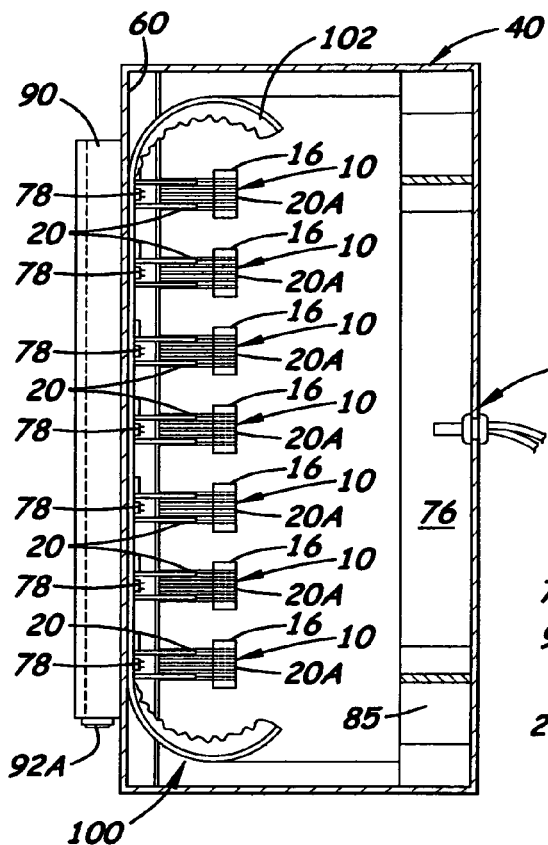
FIG. 8 is a sectional, top plan view of the lighthouse.
Figure 10:
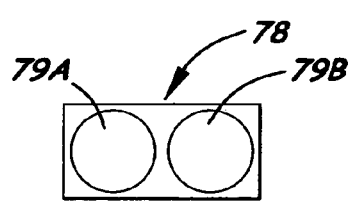
FIG. 10 is a front plan view of the near infrared light source.
Figure 9:
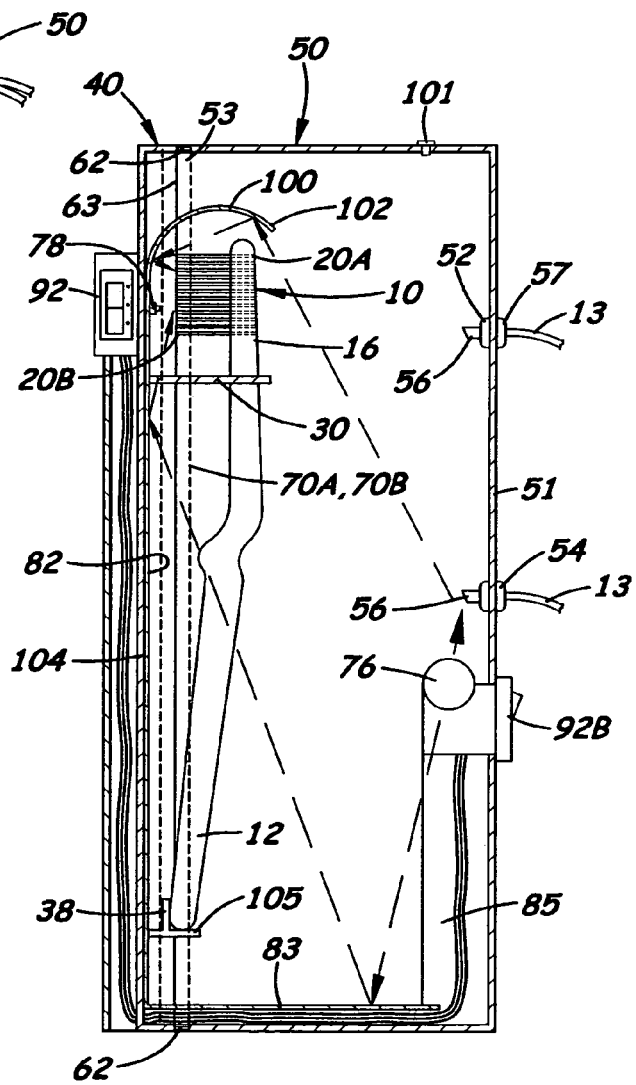
FIG. 9 is a sectional, right side elevational plan view of the lighthouse.
Figure 11:
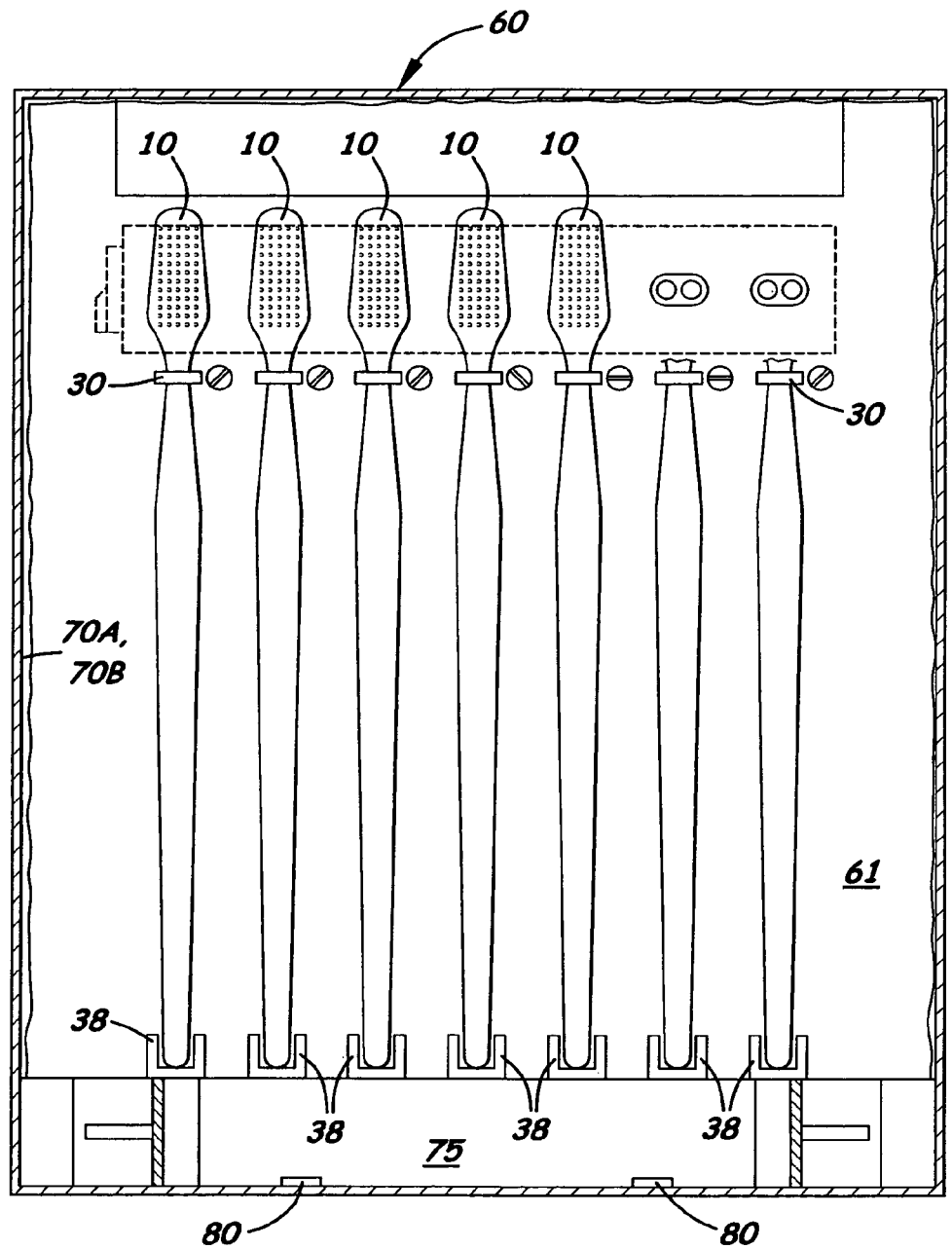
FIG. 11 is a sectional, front elevational view of the lighthouse.

An ultraviolet light source or an optical near infrared light source are used to deliver ultraviolet light or near infrared light, respectively, to the toothbrush 110. In the first embodiment, the ultraviolet light source is identical to the ultraviolet light source described in the inventor's earlier filed utility patent application (Ser. No. 10/865,877; filed June 14, 2004; and entitled Germicidal Toothbrush and Holder). The ultraviolet light source includes an ultraviolet lamp 76 shown more clearly in FIGS. 8–10 mounted inside a rectangular-shaped main body 50 and a closable door 60. The main body 50 is approx. 3 inches by 6 inches by 9 inches (W×L×H), and the door 60 is approximately the same width and height and approximately ½ inch in depth. Hinges 62 are disposed between the adjacent edges of the main body 50 and door 60 that allows the door 60 to be selectively opened and closed. Disposed between the perimeter edges 53, 63 of the main body 50 and the door 60, respectively, are interlocking male and female seals 70A, 70B, respectively, that prevents light from escaping between the adjoining edges 53, 63 of the main body 50 and door 60 when the door 60 is closed.

In the preferred embodiment, a plurality of optical fiber toothbrushes 10 is mounted on the inside surface of the door 60. Mounted behind the toothbrushes 10, is a longitudinally aligned reflector 100. The reflector 100 includes an upper concave section 102 that surrounds the heads of the toothbrushes 10, a flat intermediate section 104 that extends downward behind the handles 12, and a lower section 105 that is perpendicular aligned with the intermediate section 104 that extends forward beyond the ends of the handles 12. The ultraviolet lamp 76 is mounted inside the body 50 so that light rays from the lamp 76 are transmitted directly to the proximal ends 20B of the toothbrushes 10 or reflected off the various sections 102, 104, 105 of the reflector 100 and towards the distal ends 20A of the bristles 20 that extend inward towards the reflector 100.

Each toothbrush 10 is attached to the inside surface 61 of the door 60 with spring clamp retainer 30. In the first embodiment shown in FIGS. 1–3, there are seven spring clamp retainers 30 that securely hold seven, parallel toothbrushes 10 in a longitudinally aligned position in the inside surface 61 of the door 60. FIG. 12 is a detailed top plan view of a spring clamp retainer 30 that allow easy insertion and extraction of a toothbrush 10 with slight rotational adjustment. Each spring clamp retainer 30 includes a fixed arm 31 perpendicular aligned and extending inward from the inside surface 61 of the door 60. A screw 37 is used to securely attach the fixed arm 31 to the inside surface 61. Attached to the distal end of the fixed arm 31 is a short cross member 32. Attached to the cross member 32 is an inward extending T-shaped peg 36. Formed on each toothbrush head 16 is a small hole 11 designed to receive the peg 36.

Aligned parallel to the fixed arm 31 is a spring arm 34. Attached to the distal end of the spring arm 34 is a diagonally aligned latch 39 that extends over the outer edge of the toothbrush 10 when the toothbrush head 16 is properly position on the retainer 30 and attached to the peg 37 to hold the toothbrush head 16 on the spring clamp retainer 30.

Located below each spring clamp receiver 30 and also attached to the inside surface 61 of the door 60 is a U-shaped brush holder 38. During use, the brush holder 38 receives the flat distal end of the toothbrush 10. After seating the bottom end of the toothbrush 10 into the brush holder 38, the side of the neck of the toothbrush 10 is placed against the cross member 32 on the fixed arm 31. The other side of the neck brushes against the sloping edge of the latch 39 on the spring arm 34. Once placed in position, the toothbrush 10 is then pressed inward so that the peg 36 extends into the hole 11. The toothbrush head 16 is then in proper position.

In the preferred embodiment, the ultraviolet lamp 76 is germicidal. Ultraviolet light is divided into three sections according to wavelength. UV-C includes wavelengths from 100 nm to 280 nm, UV-B includes wavelengths from 280 nm to 315 nm, while UV-A includes wavelengths form 315 nm to 400 nm. The lamp 76 produces primarily UV-C light that is germicidal and deactivates DNA of bacteria and viruses and so destroys their ability to multiply and cause disease. It specifically damages the nucleic acid of organisms by forming covalent bonds to adjacent bases in the DNA. The formation of such bonds prevents the DNA from unzipping during replication and the organism is unable to reproduce.

As stated above, the ultraviolet lamp 76 is mounted on the inside surface of the main body 50 opposite one or more of the toothbrushes 10. In the embodiment shown herein, the ultraviolet lamp 76 measures approximately 6 inches in length including the end connectors, and ½ inch in diameter. The ultraviolet lamp 76 is longitudinally aligned and attached to the back wall 51 of the main body 50 opposite the door 60 with screws. It is designed to be moved to different positions on the back wall 51 by adjusting the screws. Typically, the ultraviolet lamp 76 is set in its proper position by the manufacturer.

Also located inside the main body 50 is at least one near infrared light source 78. In the preferred embodiment, the near infrared light source 78 is located inside the main body 50 so that near infrared light is transmitted to each toothbrush head 16. In the preferred embodiment, shown in FIG. 10, the near infrared light source 78 is a pair of LED bulbs 79A, 79B centrally mounted on the surface of the main body 50 facing the bristles 20 of each toothbrush 10. In the preferred embodiment, one LED bulb 79A transmits light at a wavelength of approximately 650 nm. and the other LED bulb 79B transmits light at a wavelength of approximately 800 nm.

Mounted on the near surface of the main body 50 is an extension box 90 upon which a three-way switch 92 is mounted. One pole of the switch 92A is electronically connected to the two LED bulbs 79A, 79B. The second pole of the switch 92B is connected to the ultraviolet lamp 76.

Mounted on the front surface of the main body 50 is an ultraviolet light conduit connector port 52 and a near-infrared conduit connector port 54. The ultraviolet light conduit connector port 52 is connected to a short section 32 of optical fiber that terminates inside the main body 50 adjacent to the ultraviolet lamp 76. The end of the short section 53 maybe cut at an angle (45°) so that ultraviolet light may be internally reflected. Attached to the opposite, distal end of the short section 53 is a coupler 138 that attaches to the primary optical fiber 113 that connects to the main optical fiber 122 located inside the germicidal toothbrush 110.

The near-infrared conduit connector port 54 is mounted on the front surface of the main body 50 directly across from the two LED bulbs 79A, 79B. The port 52 also includes a short section of optical fiber 56 that terminates inside the main body 50 and extends outward. Attached to the distal end of the short section of optical fiber 56 is a second coupler (not shown) that also may be connected to the main optical fiber 122 in the germicidal toothbrush 110.

A timer 85 is mounted on the outside of the main body 50 and used to control the length of time each light source 76 or 78 is lit. Typically, about 60 seconds is all that is needed to completely sterilize the heads 16 and bristles 20 and the gum tissue. However, if the toothbrushes 10 and 110 are wet additional time may be needed. The timer 85 automatically turns off the light source 76 or 78 at a predetermine length of time.

As an alternate embodiment, one or more infrared light sources 78 are located inside a separate main body 50' and not in the main body 50 that houses the ultraviolet light source. Like the main body 50, the near infrared light source 78 is also a pair of LED bulbs 80A, 80B centrally mounted in the main body 50' and facing the bristles 20 of each toothbrush. In the main body 50' no ultraviolet light source is provided.

Also with each embodiment, a light peephole 101 is provided on the side of the main body 50 that enables the user to determine if the lamp 76 or bulbs 79A, 79B are working and not burned out. The peephole 101 is covered with suitable cover to prevent any germicidal or near infrared light from escaping.

An electrical plug 112 and wires 113, 115 are connected to a 24 volt transformer 117 to provide electrical power to the main body 50 and to the handpiece 110, respectively, and the bulbs 79A, 7913. Mounted on the side of the transformer 117 is a cutoff switch 120 that prevents the lamp 76 and bulbs 79A, 79B from being activated if the door 60 on the main body 50 is open or ajar and not sealed.

In compliance with the statute, the invention described herein has been described in language more or less specific as to structural features. It should be understood, however, that the invention is not limited to the specific features shown, since the means and construction shown is comprised only of the preferred embodiments for putting the invention into effect. The invention is therefore claimed in any of its forms or modifications within the legitimate and valid scope of the amended claims, appropriately interpreted in accordance with the doctrine of equivalents.

I claim:

1. An optical fiber toothbrush with bristles, comprising:
   a. a handle;
   b. a toothbrush head attached to said handle, said toothbrush head including a longitudinal axis and an inner cavity;
   c. a main optical fiber that extends longitudinally inside said handle and into said inner cavity in said toothbrush head;
   d. a plurality of bristles each made of at least one optical fiber capable of transmitting light, each said bristle extends from said toothbrush head and includes a proximal end that extends into said inner cavity, said distal end of said bristle being aligned with the end of said main optical fiber so that light transmitted through said main optical fiber is transmitted to said proximal end of said bristles; and,
   e. means for moving said proximal ends of said bristles longitudinally inside said toothbrush head so that said bristles reciprocating in fore and aft directions on said toothbrush head.

2. The toothbrush as recited in claim 1, wherein said means for moving said proximal ends of said bristles inside said toothbrush head is a longitudinally aligned bar coupled to an electric motor located inside said handle.

3. The toothbrush as recited in claim 2, further including a battery located inside said handle and connected to said electric motor to provide an electric current thereto.

4. The toothbrush as recited in claim 2, further including a switch mounted on said handle and coupled to said electric motor enabling said electric motor to be turned on or off.

5. The toothbrush as recited in claim 3, further including a switch mounted on said handle and coupled to said electric motor enabling said electric motor to be turned on or off.

6. The toothbrush as recited in claim 1, wherein said toothbrush head is removably connected to said handle.

7. The toothbrush as recited in claim 2, further including a connecting rod connected to said bar, a pinion gear connected to said electric motor and a main gear used to couple said rotational movement of said pinion gear to said connecting rod, said connecting rod able to move longitudinally inside said toothbrush when said main gear is rotated.

8. The toothbrush as recited in claim 1, further including a light box with a near infrared light source located therein and a primary fiber optic that extends between said light box and said main optical fiber in said toothbrush.

9. The toothbrush as recited in claim 1, further including a near infrared light source located inside said light box to provide near infrared light to said bristles in said toothbrush.

10. The toothbrush as recited in claim 2, further including a light box with an ultraviolet light source located therein and a primary fiber optic that extends between said light box and said main optical fiber in said toothbrush.

11. The toothbrush as recited in claim 6, further including a light box with a near infrared light source located therein and a primary fiber optic that extends between said light box and said main optical fiber in said toothbrush.

12. The toothbrush as recited in claim 10, further including a near infrared light source located inside said light box to provide near infrared light to said bristles in said toothbrush.

13. The toothbrush as recited in claim 3, further including a light box with an ultraviolet light source located therein, and a primary fiber optic that extends between said light box and said main optical fiber in said toothbrush.

14. The toothbrush as recited in claim 3, further including a light box with a near infrared light source located therein and a primary fiber optic that extends between said light box and said main optical fiber in said toothbrush.

15. The toothbrush as recited in claim 13, further including a near infrared light source
located inside said light box to provide near infrared light to said bristles in said toothbrush.

16. The toothbrush as recited in claim 5, further including a light box with an ultraviolet light source located therein, and a primary fiber optic that extends between said light box and said main optical fiber in said toothbrush.

17. The toothbrush as recited in claim 5, further including a light box with a near infrared light source located therein and a primary fiber optic that extends between said light box and said main optical fiber in said toothbrush.

18. The toothbrush as recited in claim 16, further including a near infrared light source located inside said light box to provide near infrared light to said bristles in said toothbrush.

* * * * *